United States Patent
Ginosar et al.

(10) Patent No.: US 7,514,575 B2
(45) Date of Patent: Apr. 7, 2009

(54) PRODUCTION OF BIODIESEL USING EXPANDED GAS SOLVENTS

(75) Inventors: Daniel M. Ginosar, Idaho Falls, ID (US); Robert V. Fox, Idaho Falls, ID (US); Lucia M. Petkovic, Idaho Falls, ID (US)

(73) Assignee: Battelle Energy Allicance, LLC, Idaho Falls, ID (US)

( * ) Notice: Subject to any disclaimer, the term of this patent is extended or adjusted under 35 U.S.C. 154(b) by 493 days.

(21) Appl. No.: 11/123,607

(22) Filed: May 6, 2005

(65) Prior Publication Data
US 2006/0252950 A1 Nov. 9, 2006

(51) Int. Cl.
*C11C 1/00* (2006.01)
*C11C 3/00* (2006.01)
(52) U.S. Cl. ...................................................... 554/169
(58) Field of Classification Search ................... 554/169
See application file for complete search history.

(56) References Cited

U.S. PATENT DOCUMENTS

| | | | |
|---|---|---|---|
| 3,436,344 A | 4/1969 | Canning et al. | |
| 4,164,506 A | 8/1979 | Kawahara et al. | |
| 4,695,411 A | 9/1987 | Stern et al. | |
| 4,698,186 A | 10/1987 | Jeromin et al. | |
| 4,792,418 A | 12/1988 | Rubin et al. | |
| 4,839,287 A | 6/1989 | Holmberg et al. | |
| 5,124,026 A | 6/1992 | Taylor et al. | |
| 5,219,744 A | 6/1993 | Kurashige et al. | |
| 5,242,578 A | 9/1993 | Taylor et al. | |
| 5,288,619 A | 2/1994 | Brown et al. | |
| 5,424,466 A | 6/1995 | Stern et al. | |
| 5,424,467 A | 6/1995 | Bam et al. | |
| 5,480,787 A | 1/1996 | Negishi et al. | |
| 5,481,058 A | 1/1996 | Blackwell et al. | |
| 5,520,708 A | 5/1996 | Johnson et al. | |
| 5,525,126 A | 6/1996 | Basu et al. | |
| 5,578,090 A | 11/1996 | Bradin | |

(Continued)

FOREIGN PATENT DOCUMENTS

JP 63-112536 5/1988

(Continued)

OTHER PUBLICATIONS

International Search Report dated Nov. 4, 1999 (2 pages).

(Continued)

*Primary Examiner*—Deborah D Carr
(74) *Attorney, Agent, or Firm*—Trask Britt

(57) ABSTRACT

A method of producing an alkyl ester. The method comprises providing an alcohol and a triglyceride or fatty acid. An expanding gas is dissolved into the alcohol to form a gas expanded solvent. The alcohol is reacted with the triglyceride or fatty acid in a single phase to produce the alkyl ester. The expanding gas may be a nonpolar expanding gas, such as carbon dioxide, methane, ethane, propane, butane, pentane, ethylene, propylene, butylene, pentene, isomers thereof, and mixtures thereof, which is dissolved into the alcohol. The gas expanded solvent may be maintained at a temperature below, at, or above a critical temperature of the expanding gas and at a pressure below, at, or above a critical pressure of the expanding gas.

26 Claims, 1 Drawing Sheet

U.S. PATENT DOCUMENTS

| | | | |
|---|---|---|---|
| 5,599,358 | A | 2/1997 | Giavazzi et al. |
| 5,697,986 | A | 12/1997 | Haas |
| 5,713,965 | A | 2/1998 | Foglia et al. |
| 5,783,243 | A | 7/1998 | Benado |
| 6,201,144 | B1 | 3/2001 | Isbell et al. |
| 6,288,251 | B1 | 9/2001 | Tsuto et al. |
| 6,399,800 | B1 | 6/2002 | Haas et al. |
| 6,524,469 | B1 | 2/2003 | Schucker |
| 6,570,030 | B2 | 5/2003 | Goto et al. |
| 6,712,867 | B1 | 3/2004 | Boocock |
| 6,887,283 | B1 * | 5/2005 | Ginosar et al. ............ 44/388 |
| 2004/0087809 | A1 | 5/2004 | Nakayama et al. |

FOREIGN PATENT DOCUMENTS

| | | |
|---|---|---|
| JP | 07-062385 | 3/1995 |
| JP | 09-157684 | 12/1995 |
| JP | 2000-270886 | 3/1999 |
| WO | WO 00/05327 | 2/2000 |

OTHER PUBLICATIONS

Bernard et al., "Internal Mass Transfer Limitation During Enzymatic Esterification in Supercritical Carbon Dioxide and Hexane, Biocatalysis and Biotransformation," vol. 12, (1995) pp. 299-308.

Cernia et al., "Lipases in Supercritical Fluids," Lipases PT B Methods in Enzymology, vol. 286, pp. 495-508 (1997).

Cernia et al. "The Role of the Reastion Medium in Lipase-catalyzed Esterifications and Transesterificatins," Chemistry and Physicas of Lipids, vol. 93, Nos. 1-2, pp. 157-168, Jun. 1998.

Chi et al., "Enzymatic Interesterification in Supercritical Carbondioxide," Agricultural and Biological Chemistry, vol. 52, No. 6, pp. 1541-1550, Jun. 1988.

Colombie et al., "Water Activity Control: A Way To Improve the Efficiency of Continuous Lipase Esterification," Biotechnology And Bioengineering, vol. 60, No. 3, pp. 362-368, Nov. 5, 1998.

Demirbas, Ayhan, "Biodiesel from vegetable oils via transesterification in supercritical methanol," Energy Conversion and Management 43 (2002) 2349-2356.

Demirbas, Ayhan, "Biodiesel fuels from vegetable oils via catalytic and non-catalytic supercritical alcohol transesterifications and other methods: a survey," Energy Conversion and Management 44 (2003) 2093-2109.

Dumont et al., "Continuous Synthesis of Ethyl Myristate By Enzymatic Reaction in Supercritical Carbon Dioxide," Journal of Supercritical Fluids, vol. 6, No. 2, pp. 85-89, Jun. 1993.

Fukuda et al., "Biodiesel Fuel Production by Transesterification of Oils," Journal of Bioscience and Bioengineering, vol. 92, No. 5, 405-416, 2001.

Gunnlaugsdottir et al., "Process Parameters Influencing Ethanolysis of Cod Liver Oil in Supercritical Carbon Dioxide," Journal of Supercritical Fluids, vol. 12, No. 1, pp. 85-93, Mar. 15, 1998.

Gunnlaugsdottir et al., "Alcoholysis and Glyceride Synthesis with Immobilized Lipase on Controlled-pore Glass of Varying Hydrophobicity in Supercritical Carbon Dioxide," Enzyme and Microbial Technology, vol. 22, No. 5, pp. 360-367, Apr. 1998.

Hrnjez et al., "Enzymatic Esterification of 1,2-Butanediol and 1,3 Butanediol in Supercritical Carbon-Dioxide Reaction Rate, Regioselectivity, and Stereoselectivity as a Function of Pressure," Abstracts of Papers of the American Chemical Society 207:315-ORGN, Part 2 Mar. 13, 1994.

Habulin et al., "Synthesis of Oleic Acid Esters Catalyzed by Immobilized Lipase," Journal of Agricultural and Food Chemistry, vol. 44, No. 1, pp. 338-342, Jan. 1996.

Hyatt, John A., "Liquid and Supercritical Carbon Dioxide as Organic Solvents," Journal of Organic Chemistry, vol. 49, No. 26, pp. 5097-5101, 1984.

Ikariya et al., "Chemical Reactions in Supercritical Fluids," Journal of Synthetic Organic Chemistry Japan, vol. 53, No. 5, pp. 358-369, May 1995.

Ikushima, Yutaka, "Supercritical Fluids: An Interesting Medium for Chemical and Biochemical Processes, Advances in Colloid and Interface Science," vol. 71-71, 259-280, Sep. 1, 1997.

Ikushima et al., Promotion of A Lipase-Catalyzed Esterification In Supercritical Carbon Dioxide In The Near-Critical Region, Chemical Engineering Science vol. 51, No. 11, pp. 2817-2822, Jun. 1996.

Ikushima et al., "Promotion of Lipase-catalyzed Esterification of N-Valeric Acid and Citronellol In Supercritical Carbon Dioxide in the Near-critical Region," Journal of Chemical Engineering of Japan, vol. 29, No. 3, pp. 551-553, Jun. 1996.

Jackson, et al., "Methanolysis of Seed Oils in Flowing Supercritical Dioxide," Journal of the American Oil Chemists Society, vol. 73, No. 3 (1996).

Kiran et al. "Supercritical Fluid Engineering Science Fundamentals and Applications," pp. 200-219.

Knez et al., "Enzyme Catalyzed Reactions in Dense Gases," vol. 14, No. 1, pp. 17-29, Oct. 1, 1998.

Knez et al., "Enzymatic Synthesis of Oleyl Oleate in Dense Fluids," Journal of the American Oil Chemists Society, vol. 72, No. 11, Nov. 1995, pp. 1345-1349.

Knez et al., "Lipase Catalysed Esterification At High Pressure," Biotechnology and Bioengineering, vol. 9, (1994) pp. 115-121.

Krmelj et al., "Lipase-catalyzed synthesis of Oleyl Oleate in Pressurized and Supercritical Solvents," FETT-Lipid, vol. 101, No. 1, pp. 34-38, Jan. 1999.

Kusdiana et al., "Kinetics of transesterification in rapeseed oil to biodiesel fuel as treated in supercritical methanol," Fuel 80 (2001) 693-698.

Lopez-Belmonte et al., "Enantioselective Esterification of 2-Arylpropionic Acids Catalyzed By Immobilized Rhizomucor Miehei Lipase," Journal of Organic Chemistry, vol. 62, No. 6, pp. 1831-1840, Mar. 21, 1997.

Ma, Fangrui et al., "Biodiesel Production: A Review," Bioresource Technology, vol. 70, No. 1, pp. 1-15, Oct. 1999.

March, Jerry, "Advanced Organic Chemistry, Reactions, Mechanisms, and Structure," 4th Edition, John Wiley & Sons, 1992, pp. 393-396.

Marty et al., "Kinetics of Lipase-Catalyzed Esterification in Supercritical CO2," Biotechnology and Bioengineering, vol. 39, pp. 273-280 (1992).

Marty et al., "Continuous Reaction-Separation Process for Enzymatic Esterification in Supercritical Carbon Dioxide," Biotechnology and Bioengineering, vol. 43, No. 6, pp. 497-504, Mar. 15, 1994.

Marty et al., "Comparison of Lipase-catalysed Esterification in Supercritical Carbon Dioxide and in n-Hexane," Biotechnology Letters, vol. 12, No. 1, pp. 11-16, Jan. 1990.

McDaniel et al., "Esterification of Decanoic Acid During Supercritical Fluid Extraction Employing Either Methanol-modified Carbon Dioxide or a Methanol Trap," Journal of Chromatography, vol. 858, No. 2, pp. 201-207, Oct. 15, 1999.

Mensah et al., "Adsorptive Control of Water in Esterification with Immobilized Enzymes: I. Batch Reactor Behavior," Biotechnology and Bioengineering, vol. 60, No. 4, pp. 434-444, Nov. 20, 1998.

Mesiano et al., Chemical Reviews, vol. 99, No. 2, pp. 623-633, Feb. 1999.

Michor et al., "Enzymatic Catalysis in Supercritical Carbon Dioxide: Comparison of Different Lipases and a Novel Esterase," Biotechnology Letters, vol. 18, No. 1, pp. 79-84, Jan. 1996.

Mori et al., "Biocatalytic Esterification in Supercritical Carbon Dioxide by Using a Lipid-coated Lipase," Chemistry Letters, vol. 9, 921-922, Sep. 1998.

Murakata et al., "Esterification Activity of Lipasse Entrapped in Reverse Micelles Formed in Liquefied Gas," Journal of Chemical Engineering of Japan, vol. 29, No. 2, pp. 277-281, Apr. 1996.

Nilsson et al., "Solubilities of Mehtyl Oleate, Oleic Acid, Oleyl Glycerols, and Oleyl Glycerol Mixtures in Supercritical Carbon Dioxide," Journal of the American Oil Chemists Society, JAOCS, vol. 68, No. 2, Feb. 1991, pp. 87-91.

Pasta et al., "Subtilisin-catalyzed Transesterification in Supercritical Carbon Dioxide," Biotechnology Letters, vol. 11, No. 9, pp. 643-648 (1989).

Saka et al., "Biodiesel fuel from rapeseed oil as prepared in supercritical methanol," Fuel 80 (2001) 225-231.

Sarkari et al., "Enzymatic Catalysis in Cosolvent Modified Pressurized Organic Solvents," Biotechnology and Bioengineering, vol. 65, No. 3, pp. 258-264, Nov. 5, 1999.

Stamatis et al, "Studies on the Enzymatic Synthesis of Sugar Esters in Organic Medium and Supercritical Carbon Dioxide," Chemical and Biochemical Engineering Quarterly, vol. 12, No. 3, pp. 151-156, Sep. 1998.

Savage et al., "Reactions at Supercritical Conditions: Applications and Fundamentals," Aiche Journal, vol. 41, No. 7, pp. 1723-1778, Jul. 1995.

Stransky et al., "Simple Quantitative Transesterification of Lipids," FETT-Lipid, vol. 98, No. 2, 65-71, Feb. 1996.

Subramaniam et al., "Reactions in Supercritical Fluids—A Review," Industrial & Engineering Chemistry Process Design and Development, vol. 25, No. 1, 1-12, Jan. 1986.

Vieville et al, "Esterification of Oleic Acid by Methanol Catalyzed by p-Toluenesulfonic Acid and the Cation-Exchange Resins K2411 and K1481 in Supercritical Carbon Dioxide," Industrial & Engineering Chemistry Research, vol. 32, No. 9, pp. 2065-2068, Sep. 1993.

Vija et al, "Lipase-catalysed Esterification in Supercritical Carbon Dioxide and In Hexane," Bioorganic & Medicinal Chemistry Letters, vol. 7, No. 3, pp. 259-262, 1997.

Wu et al., "Enhancement of Enantioselectivity by Altering Alcohol Concentration for Esterification in Supercritical CO2," Journal of Chemical Engineering of Japan, vol. 32, No. 3, pp. 338-340, Jun. 1999.

Yahya et al., "Ester Synthesis in Lipase-catalyzed Reactions," Enzyme and Microbial Technology, vol. 23, Nos. 7-8, pp. 438-450, Dec. 15, 1998.

Yoon et al., "Transesterification between Triolein and Ethylbehenate by Immobilized Lipase in Supercritical Carbon Dioxide," Journal of Fermentation and Bioengineering, vol. 82, No. 4, 334-340, Jun. 1996.

Yu et al., "Enzymatic Esterification of Fatty Acid Mixtures from Milk Fat and Anyhydrous Milk Fat with Canola Oil in Supercritical Carbon Dioxide," Biotechnology Progress, 1992, vol. 8 No. 6, 508-513.

Yu et al., "Enzymatic Reaction in Supercritical Fluid Carbon Dioxide Using Dry-Ice," Journal of the Chinese Chemical Society, vol. 46, No. 5, pp. 647-650, Oct. 1999.

Gunnlaugsdottir et al., "Lipase-Catalyzed Alcoholysis with Supercritical Carbon Dioxide Extraction 2: Phase Behavior," Journal of the American Oil Chemists Society, vol. 74, No. 11, pp. 1491-1494, Nov. 1997.

* cited by examiner

PRODUCTION OF BIODIESEL USING EXPANDED GAS SOLVENTS

GOVERNMENT RIGHTS

The United States Government has certain rights in this invention pursuant to Contract No. DE-AC07-05ID14517 between the United States Department of Energy and Battelle Energy Alliance, LLC.

FIELD OF THE INVENTION

The present invention relates to a method of improving a rate of a transesterification or esterification reaction used in producing biodiesel and subsequent downstream separation of the biodiesel. More specifically, the present invention relates to using a gas expanded solvent to improve the rate of the reaction and the subsequent downstream separation.

BACKGROUND OF THE INVENTION

Biodiesel has been the subject of much investigation as an alternative for petroleum diesel fuel. As used herein, the term "biodiesel" refers to an ester-based fuel oxygenate that is derived from a biological source. The biodiesel is used as an alternative for, or as an additive to, petroleum diesel fuel in automobiles or other vehicles. The biodiesel is typically produced from a triglyceride starting material or a fatty acid starting material by a transesterification reaction or an esterification reaction, respectively. Generally, the triglyceride is reacted, or transesterified, with an alcohol to produce glycerol (also known as glycerin) and a corresponding alkyl ester of the triglyceride. Similarly, the fatty acid is reacted, or esterified, with an alcohol to produce a corresponding alkyl ester of the fatty acid. Large amounts of the triglyceride and fatty acid starting materials are available from inexpensive sources, such as fats or oils. However, since these fats or oils are too viscous to use directly as the biodiesel fuel, the triglycerides or fatty acids are transesterified or esterified to produce the corresponding alkyl ester, which has a lower viscosity than that of the starting material. As such, the corresponding alkyl ester is able to be used as the biodiesel fuel.

The transesterification of the triglyceride (or the esterification of the fatty acid) is conducted with an excess of the alcohol in the presence of a catalyst. Since the alcohol is immiscible with the triglyceride or the fatty acid starting material, a rate of the reaction is limited by the mixing rate of the starting materials. As the transesterification reaction proceeds, two products are formed, the alkyl ester and the glycerol. One phase includes the alkyl ester and the other phase includes the glycerol. The liquid phases are allowed sufficient time to settle and separate before additional processing steps are conducted to purify the alkyl ester from the glycerol. If large amounts of glycerol remain in the alkyl ester phase, the quality of the biodiesel fuel is diminished. Similarly, the quality of the glycerol is diminished if the glycerol is contaminated with the alkyl ester. Significant problems arise in separating the two phases because the phases are separated by gravity and the separation produces large amounts of waste water, which adds to the cost and complexity of the process. The process is also long and requires numerous hours to process each batch of the triglyceride or the fatty acid starting material.

To improve the reaction rate, supercritical fluids have been used to dissolve the starting materials into a single critical phase. As disclosed in International Application WO 00/05327 to Ginosar et al., the alcohol and the triglyceride (or the fatty acid) are solvated in a critical fluid, which provides a single phase in which the reaction occurs. However, in order for the reaction to proceed, the temperature and pressure conditions must be sufficiently high to maintain the fluid in the critical phase. Therefore, the reaction requires elevated temperatures, pressures, and/or solvent flows.

It would be desirable to increase the rate of the transesterification reaction or esterification reaction and to improve the separation of the alkyl ester from other products of the reaction.

BRIEF SUMMARY OF THE INVENTION

The present invention relates to a method of producing an alkyl ester. The method comprises providing a reaction mixture comprising an alcohol and a triglyceride or fatty acid. Each of the alcohol and the triglyceride or fatty acid may be provided in a liquid phase. An expanding gas is dissolved into the alcohol. The alcohol is reacted with the triglyceride or fatty acid in a single phase to produce the alkyl ester. The expanding gas may be a nonpolar expanding gas that is dissolved into the alcohol. The nonpolar expanding gas may be selected from the group consisting of carbon dioxide, methane, ethane, propane, butane, pentane, ethylene, propylene, butylene, pentene, isomers thereof, and mixtures thereof. The reaction mixture may be maintained at a temperature below, at, or above a critical temperature of the expanding gas and at a pressure below, at, or above a critical pressure of the expanding gas. For instance, the temperature of the reaction mixture may be maintained from approximately 10° C. to approximately 200° C. The pressure of the reaction mixture may be maintained at from approximately 200 pounds per square inch gauge ("psig") to approximately 5,000 psig.

At least one of the temperature and pressure may be adjusted, such as by lowering, to separate the alkyl ester from at least one of the expanding gas, glycerol, and excess alcohol. At least one of the temperature and pressure may also be adjusted, such as by lowering at least one of the temperature and pressure to ambient temperature and ambient pressure, to recover the expanding gas.

The present invention also relates to a method of producing an alkyl ester that comprises dissolving an expanding gas into an alcohol to form a gas expanded solvent, contacting the gas expanded solvent with a triglyceride or a fatty acid, and reacting the alcohol and the triglyceride or fatty acid in a single phase to form the alkyl ester.

BRIEF DESCRIPTION OF THE DRAWING

While the specification concludes with claims particularly pointing out and distinctly claiming that which is regarded as the present invention, the advantages of this invention may be more readily ascertained from the following description of the invention when read in conjunction with the accompanying drawing in which:

DETAILED DESCRIPTION OF THE INVENTION

Figure 1:
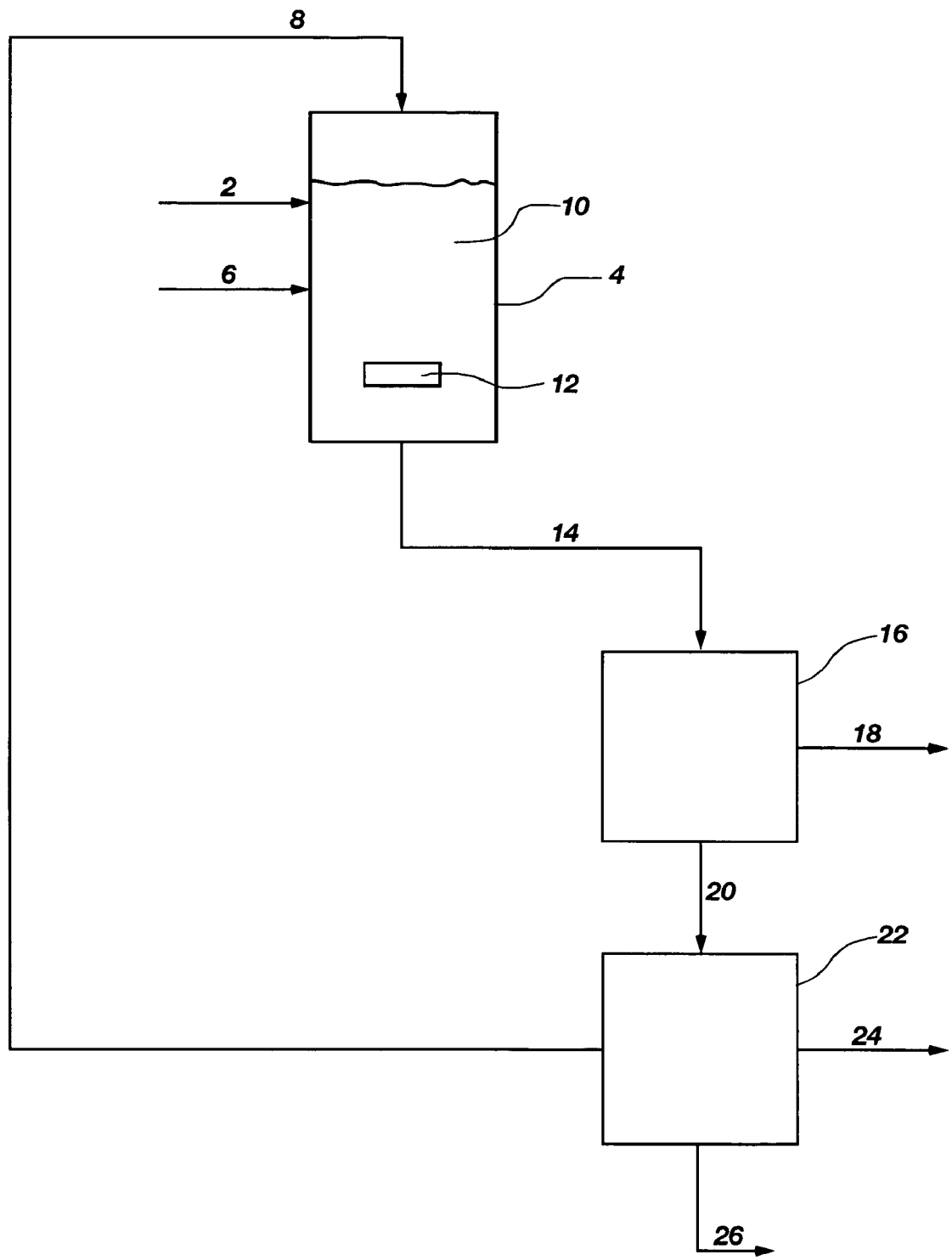
FIG. 1 is a schematic illustration of an embodiment of a system for producing the alkyl ester according to the present invention.

A gas expanded solvent is used to improve a rate of a reaction for producing biodiesel. The gas expanded solvent also provides a method of improving product quality of an esterification reaction or transesterification reaction that produces biodiesel. As used herein, the term "gas expanded solvent" refers to a liquid in which a quantity of expanding gas is dissolved. The gas expanded solvent is also used to improve separation of the biodiesel from other products of the reaction. By dissolving the expanding gas into the liquid, a volume of the liquid may be increased and properties of the gas expanded solvent may be altered so that the rate of the reaction is increased. The expanding gas may subsequently be recovered from the gas expanded solvent to aid in separating the biodiesel from the other reaction products.

The biodiesel produced using the gas expanded solvent may be an alkyl ester or a mixture of alkyl esters, depending on a purity of starting materials that are used. The biodiesel may be a mixture of alkyl esters, which depends on the source of the oil used as the starting material. Therefore, as used herein, the term "alkyl ester" encompasses a single type of alkyl ester or a mixture of different types of alkyl esters. An alkyl ester of a glyceride may be produced by a transesterification reaction in which an alcohol is reacted with a glyceride. Alternatively, an alkyl ester of a fatty acid may be produced by an esterification reaction in which an alcohol is reacted with a fatty acid. Each of the alcohol and the triglyceride or fatty acid is present in a liquid phase in the reaction. The chemical reaction for producing the alkyl ester is shown in Equation 1:

$$R_1COOR_2 + R_3OH \rightarrow R_1COOR_3 + R_2OH \quad \text{(Equation 1)}.$$

In the reaction, the organic ester, $R_1COOR_2$, is reacted with the alcohol, $R_3OH$, to produce the organic ester, $R_1COOR_3$, and the alcohol, $R_2OH$. $R_1$ may be an aliphatic hydrocarbon chain having from four to thirty-six carbon atoms. $R_2$ may be glycerol or another aliphatic hydrocarbon chain having from four to thirty-six carbon atoms. $R_2$ is linked to $R_1$ through an ester ("COO$^-$") linkage. $R_1COOR_2$ may be an acylglycerol, fat, oil, wax, or fatty acid. The acylglycerol may be mono-, di-, or tri-substituted including, but not limited to, a monoglyceride, diglyceride, or triglyceride. If $R_1COOR_2$ is a monoglyceride, diglyceride, triglyceride, fat, or oil, $R_1$ may be the aliphatic hydrocarbon ($C_4$ to $C_{36}$) chain and $R_2$ may be glycerol. If $R_1COOR_2$ is a fatty acid, $R_1$ may be the aliphatic hydrocarbon ($C_4$ to $C_{36}$) chain and $R_2$ may be hydrogen or a metal (i.e., $R_2$ is the salt of the fatty acid ($R_1COO^-M^+$)). $R_1COOR_2$ may also include a free fatty acid ($R_1COO^-$). If $R_1COOR_2$ is a wax, $R_1$ may be an aliphatic hydrocarbon chain linked to $R_2$ through the ester linkage. In one embodiment, $R_1COOR_2$ is a triglyceride, such as a triglyceride from vegetable oil, soybean oil, or peanut oil. In another embodiment, $R_1COOR_2$ is a fatty acid including, but not limited to, palmitic acid, stearic acid, oleic acid, or linoleic acid. The triglyceride or the fatty acid may be obtained from an animal fat, animal oil, vegetable fat, vegetable oil, or mixtures thereof, such as rapeseed oil, sesame oil, soybean oil, coconut oil, corn oil, sunflower oil, palm oil, palm kernel oil, coconut oil, safflower oil, olive oil, linseed oil, cotton seed oil, tung oil, castor oil, beef fat, pork fat, chicken fat, fish oil, rendered fat, or mixtures thereof. The triglyceride or the fatty acid may also be obtained from waste edible oils, such as restaurant grease, household grease, waste industrial frying oil, or mixtures thereof.

$R_3$ may be a short-chain hydrocarbon group, which is attached to a hydroxyl group of the alcohol. $R_3$ may include, but is not limited to, a methyl, ethyl, propyl, or butyl group. As such, the alcohol, $R_3OH$, may include, but is not limited to, methanol, ethanol, n-propanol, isopropanol, n-butanol, isobutanol, t-butanol, or mixtures thereof. The alcohol may be selected depending on the desired products of the reaction.

The expanding gas may be dissolved into one of the liquid starting materials or reactants, such as the alcohol, the triglyceride, or the fatty acid. As such, in addition to functioning as the starting material, the alcohol, the triglyceride, or the fatty acid may also function as the liquid into which the expanding gas is dissolved. The expanding gas may be substantially soluble in the liquid. The expanding gas may also have a polarity opposite to the polarity of the liquid. Therefore, the expanding gas may alter at least one of the solubility and polarity of the liquid. The expanding gas may also increase or expand the volume of the liquid. For instance, if carbon dioxide is used as the expanding gas and is dissolved into 1 ml of methanol as the liquid, the volume of the methanol increases from 1 ml to approximately 5 ml to 10 ml. Since the expanding gas and the liquid have opposite polarities, the gas expanded solvent may have a polarity that is in-between the polarity of the expanding gas and the polarity of the liquid. In other words, the gas expanded solvent may exhibit properties similar to those of the expanding gas and to those of the liquid. As such, the gas expanded solvent may improve the miscibility of the alcohol starting material with the triglyceride or fatty acid starting material.

To make the alcohol miscible with the triglyceride or fatty acid, the expanding gas of the gas expanded solvent may be a nonpolar gas, such as carbon dioxide or a hydrocarbon gas. The hydrocarbon gas may include, but is not limited to, methane, ethane, propane, butane, pentane, isomers thereof (i.e., n-butane, isobutane, t-butane, n-pentane, isopentane, etc.) or mixtures thereof. The nonpolar gas may also include ethylene, propylene, butylene, pentene, or mixtures thereof. The expanding gas may also include a mixture of nonpolar gases, such as a mixture of carbon dioxide and at least one hydrocarbon gas. The expanding gas may be substantially soluble in the liquid, which is the alcohol in this embodiment. For instance, the solubility of the expanding gas in the liquid may range from approximately 1% by weight (wt %) to approximately 20 wt %. The liquid of the gas expanded solvent may be a polar solvent, such as a short-chain alcohol. The liquid may include, but is not limited to, methanol, ethanol, propanol, butanol, isomers thereof, or mixtures thereof. The short-chain alcohol used as the solvent may be the same or different than the alcohol used as the starting material of the reaction as long as there is sufficient alcohol present as the starting material to drive the reaction to completion. As such, the alcohol may function as the starting material, the liquid of the gas expanded solvent, or as a mixture of the starting material and the liquid of the gas expanded solvent. Since the liquid of the gas expanded solvent may include the same alcohol used as the starting material, the gas expanded solvent may replace the alcohol used in conventional transesterification or esterification reactions. The expanding gas and the liquid of the gas expanded solvent may be selected based on several factors, such as the temperature, pressure, desired reaction products, solubility of the reaction products, amount of excess alcohol needed to drive the reaction to completion, and post reaction separation processes.

Since the expanding gas is nonpolar and the alcohol is polar, the polarity of the gas expanded solvent may be intermediate, or in-between, the polarity of the expanding gas and the alcohol. As such, the expanding gas may alter the properties of the alcohol. As the alcohol of the gas expanded solvent becomes more nonpolar, the alcohol may be substantially miscible with the triglyceride or fatty acid, providing increased contact between the reactants and increasing the rate of the reaction. Therefore, the mass transport of these reactants into different liquid phases is substantially eliminated, which increases the overall rate of the reaction.

To dissolve the expanding gas into the alcohol, the expanding gas may be maintained at or near its critical temperature ("$T_c$") and critical pressure ("$P_c$") (i.e., at or near a critical point of the expanding gas). For instance, each of the temperature and pressure may be slightly below, at, or slightly above the $T_c$ and $P_c$. A temperature slightly below, at, or slightly above the $T_c$ is referred to herein as a "near critical" temperature. Similarly, a pressure slightly below, at, or slightly above the $P_c$ is referred to herein as a "near critical" pressure. The $T_c$ of the expanding gas is the temperature above which the expanding gas does not exhibit a distinct gas and liquid phase. The $P_c$ of the expanding gas is the minimum pressure need to liquefy the expanding gas at a temperature incrementally below its $T_c$. If the expanding gas is heated to a temperature above the $T_c$ and pressurized to a pressure above the $P_c$, the expanding gas is in a supercritical phase and exhibits many properties of both a gas and a liquid. These properties include, but are not limited to, density, viscosity, diffusivity, and solubility. However, the properties of the expanding gas in the critical phase may be different than the properties of the expanding gas in either the liquid phase or the gas phase. For instance, in the critical phase, the expanding gas may exhibit a viscosity that is more similar to that of a gas and a density that is more similar to that of a liquid. The expanding gas may also exhibit properties similar to the properties of the critical phase at a temperature and pressure near to, but not above, the $T_c$ and the $P_c$.

The temperature and pressure conditions used to maintain the expanding gas at or near its $T_c$ and $P_c$ (at or near its critical point) may depend on the gas used as the expanding gas. Each of the temperature and pressure may be at or above the $T_c$ and $P_c$ of the expanding gas. The temperature and pressure may also be slightly below each of the $T_c$ and $P_c$ of the expanding gas so long as the expanding gas exhibits properties similar to those in the critical phase. To keep the expanding gas at or near its $T_c$, the temperature of the expanding gas may be maintained in a range of from approximately 75° C. below the $T_c$ of the expanding gas to approximately 75° C. above the $T_c$ of the expanding gas. As used herein, a near critical temperature refers to a temperature that is greater than or equal to 0.9 times the $T_c$. For the sake of example only, the expanding gas may be maintained at a temperature ranging from approximately 10° C. to approximately 200° C. To keep the expanding gas at or near its $P_c$, the pressure of the expanding gas may range from approximately 0.1 times its $P_c$ to approximately 10 times its $P_c$. For the sake of example only, the pressure of the expanding gas may be maintained in a range of from approximately 200 psig to approximately 5,000 psig. As used herein, a near critical pressure refers to a pressure that is greater than or equal to 0.5 times the $P_c$.

To produce the alkyl ester, the gas expanded solvent and the triglyceride may be contacted in a vessel, such as a reactor. The vessel may be a batch reactor or a continuous reactor, such as a flask, steel vessel, steel pipe, static mixer, or agitation vessel, as known in the art. The vessel may be formed from glass, steel, stainless steel, nickel alloys, titanium alloys, glass lined steel, polymer lined steel, ceramic lined steel, or mixtures thereof. The vessel may be equipped with means to heat the contents of the vessel and with means to pressurize the contents of the vessel. In one embodiment, the gas expanded solvent and the triglyceride are each introduced into the vessel. In another embodiment, the alcohol and the triglyceride are introduced into the vessel and the expanding gas is dissolved into the alcohol to form the gas expanded solvent.

While the embodiments herein describe transesterification of the triglyceride to produce the alkyl ester, one of ordinary skill in the art will recognize that similar principles apply to esterifying the fatty acid to produce the alkyl ester. As shown in FIG. 1, a feed stream of the alcohol 2 may be added to a vessel 4 along with a feed stream of the triglyceride 6 to form a reaction mixture. The vessel 4 may be maintained at a temperature and pressure such that the expanding gas is below its critical point. For instance, the vessel 4 may be maintained at ambient temperature and ambient pressure or at a temperature near to, but below, the $T_c$ of the expanding gas. At this point in the reaction, the alcohol 2 and the triglyceride 6 may be substantially immiscible. At least three moles of the alcohol 2 may be added to the vessel 4 for every mole of the triglyceride 6 to enable the reaction to proceed to completion. A feed stream of the expanding gas 8 may be added to a headspace of the vessel 4, contacting the alcohol 2 and the triglyceride 6. At least one of the temperature and pressure within the vessel 4 may be adjusted, bringing the expanding gas to or near its critical point. For instance, the temperature and pressure may be increased from ambient conditions to below, at, or above the $T_c$ and $P_c$ of the expanding gas 8. Alternatively, if the expanding gas 8 is already at its $T_c$, the pressure may be increased to below, at, or above the $P_c$ of the expanding gas 8, while maintaining the temperature at or above the $T_c$ of the expanding gas 8. As such, the expanding gas 8 may dissolve into the alcohol 2, forming the gas expanded solvent. Since the expanding gas 8 changes the polarity of the alcohol 2 from polar to nonpolar, the alcohol 2 and the triglyceride 6 may become miscible and form a single phase 10 in the vessel 4. In addition to altering the solubility and polarity, the liquid phase of the alcohol 2 may also be expanded. At least a portion of the alcohol 4 of the gas expanded solvent may react with the triglyceride 6 to form the alkyl ester and the glycerol. By forming the single phase 10 using the gas expanded solvent, interphase mass transfer between the alcohol 2 and the triglyceride 6 may be eliminated, increasing the rate of the reaction.

The reaction to produce the alkyl ester may be catalyzed by a solid catalyst (a heterogenous catalyst) or a liquid catalyst (a homogenous catalyst). As such, the vessel 4 may also include a catalyst 12. The reaction may also proceed without a catalyst. However, the reaction time is substantially longer if no catalyst is used. The liquid catalyst may be an acid or a base. Examples of basic liquid catalysts include, but are not limited to, sodium hydroxide, potassium hydroxide, sodium or potassium carbonates, sodium or potassium alkoxides (sodium methoxide, sodium ethoxide, sodium propoxide, sodium butoxide, potassium methoxide, potassium ethoxide, potassium propoxide, potassium butoxide, or mixtures thereof), or mixtures thereof. The sodium or potassium alkoxides may be provided on a solid support. Examples of acidic liquid catalysts include sulfuric acid, phosphoric acid, hydrochloric acid, nitric acid, an organic sulfonic acid, or mixtures thereof. The solid catalyst may also have acidic properties or basic properties. Examples of solid catalysts include, but are not limited to, microporous crystalline solids, such as zeolites; non-crystalline inorganic oxides, such as alumina, silica, silica-alumina, boria, oxides of phosphorus, titanium dioxide, zirconium dioxide, chromia, zinc oxide, magnesia, calcium oxide, or iron oxides; or mixtures thereof. The solid catalyst may be unmodified or may be modified with chlorine, fluorine, sulfur, or mixtures thereof. The solid catalyst may also be modified with an acid or base. The solid catalyst may also be an ion exchange resin having either acidic properties or basic properties. If a solid catalyst is used, the solid catalyst may be formed into a catalytic packed bed or may float free inside the vessel 4.

If the catalyst 12 is sodium hydroxide or potassium hydroxide, the catalyst 12 may react with the alcohol, such as methanol, to produce sodium methoxide or potassium methoxide.

The sodium methoxide or potassium methoxide may react with the triglyceride to form the alkyl ester. If the catalyst 12 is the sodium or potassium alkoxide, the alkoxide may react with the triglyceride to form the alkyl ester. Hydroxide ions remaining after the reaction with the triglyceride may be neutralized to prevent corrosion.

As the reaction proceeds to completion, two liquid phases may form. One phase may include the alkyl ester and the other phase may include the glycerol. Excess alcohol and the catalyst 12, if a liquid catalyst was used, may be dispersed into both phases. If the catalyst 12 is a solid catalyst, the solid catalyst may be easily removed from the reaction, such as by filtration. Each of the reaction products and the excess alcohol may be sequentially and selectively removed by adjusting at least one of the temperature and pressure in the vessel 4 or in a separator, such as in a gravity separator. If the catalyst 12 is a liquid, the catalyst 12 may be removed by gravity separation. Alternatively, the liquid catalyst may be neutralized. A first product stream 14 that includes the glycerol, the alkyl ester, the excess alcohol, the expanding gas, and the liquid catalyst, if present, may be transferred to a first separator 16. By adjusting at least one of the temperature and pressure in the first separator 16, the solubility of the reaction products, the excess alcohol, the expanding gas, and the liquid catalyst, if present, in the first product stream 14 may be changed because the expanding gas 8 may begin to desorb from the gas expanded solvent. For instance, at least one of the temperature and pressure in the first separator 16 may be lowered. As the temperature or pressure is lowered, the least soluble product, such as the glycerol, may drop out of the first product stream 14. A glycerol-enriched stream 18 may exit the first separator 16 and may be recovered. Removing the glycerol-enriched stream 18 from the first separator 16 may enhance the reaction equilibrium by driving the reaction toward production of the alkyl ester. As such, the amount of excess alcohol used to drive the reaction to completion may be substantially reduced.

A glycerol-depleted stream 20 that includes the alkyl ester, the excess alcohol, the expanding gas, the liquid catalyst, if present, and any unreacted triglyceride 6 may be transferred to a second separator 22. For the sake of example only, the first and second separators 16,22 may be multiple, cascading separators. At least one of the temperature and pressure in the second separator 22 may be adjusted to drop out the excess alcohol from the glycerol-depleted stream 20. At this point, a small amount of the expanding gas 8 may remain in the glycerol-depleted stream 20 depending on the temperature and pressure in the vessel 4. However, any remaining expanding gas 8 may eventually desorb from the glycerol-depleted stream 20 and come to equilibrium. The excess alcohol stream 24 may be removed from the second separator 22. The excess alcohol may also be removed from the glycerol-depleted stream 20 by bubbling additional gas expanded solvent through the glycerol-depleted stream 20, which vaporizes the excess alcohol. At least one of the temperature and pressure may then be further adjusted to drop out the alkyl ester. The alkyl ester stream 26 may be removed from the second separator 22 and used as a replacement for, or as an additive to, petroleum diesel fuel. The alkyl ester may also be used as detergent surfactants, herbicides, pesticide diluents, sticking agents, or lubricating additives for hydraulic and transmission fluids. After the reaction products and the excess alcohol are removed, at least one of the temperature and pressure may be adjusted to ambient temperature and pressure, enabling the expanding gas 8 to be collected. The expanding gas 8 may be recycled and reused in subsequent reactions.

The separation of the glycerol from the alkyl ester may also occur within the vessel 4 by allowing the two phases to settle over a period of time, such as by gravity separation. The two phases may then be physically separated and each of the glycerol and the alkyl ester recovered.

Since the alcohol 2 and the triglyceride 6 are miscible in the presence of the gas expanded solvent, these reactants may remain in the liquid phase during the reaction. In other words, the alcohol 2 and the triglyceride 6 may react in the liquid phase. As such, the gas expanded solvent may enable the reaction to occur in a single phase at moderate temperatures and pressures. In contrast, the temperature and pressure conditions used in the supercritical fluid processes of the prior art are substantially higher because the reaction occurs in the supercritical phase. In addition, since both the alcohol and the triglyceride are dissolved into the supercritical fluid, large amounts of the supercritical fluid are needed in the supercritical fluid processes of the prior art. In contrast, a smaller amount of the expanding gas 8 is used in the method of the present invention because the expanding gas 8 is dissolved into one starting material, such as the alcohol. The catalyst 12 used in the method of the present invention may also be more stable because no hydroxide ions are present that remain to be neutralized. Therefore, the catalyst 12 may have an increased longevity compared to the longevity of the catalyst used in the processes of the prior art. Furthermore, since the catalyst 12 does not need to be neutralized, the reaction products are not contaminated with acids or bases.

The following examples serve to explain embodiments of the present invention in more detail. These examples are not to be construed as being exhaustive or exclusive as to the scope of this invention.

EXAMPLES

Example 1

Effects of Carbon Dioxide, Propane, or Ethane on Dissolution of Methanol in Soybean Oil A series of experiments was performed at different temperatures and different initial methanol:soybean oil ratios to determine the effect of carbon dioxide, propane, or ethane as the expanding gas on the dissolution of methanol in soybean oil. With the increase in methanol solubility in the soybean oil using the carbon dioxide, propane, or ethane, it is anticipated that reaction rates would be significantly improved.

A so-called "view-cell" was set up with an associated temperature controller and high-pressure pumps. The volume of the view-cell was approximately 3 ml. About 1.5 ml of soybean oil (purchased from ICM Biomedicals, Inc.) and about 1.5 ml of methanol (purchased from Fisher Scientific International Inc.) were loaded in the view-cell, along with a magnetic stir bar. Cell ports and both inlet and outlet valves of the view-cell were closed before stirring was started in the view-cell. The temperature in the view-cell was increased to the desired experiment temperature using an Omega temperature controller. Once the temperature selected for the experiment was reached, the inlet valve connecting the view-cell with gas admission lines was opened and the gas pressure was increased using both Isco and manual syringe pumps. The gas pressure was increased by introducing carbon dioxide, propane, or ethane into the view-cell. The gas pressure was increased to a pressure approximate to the first desired pressure. The pressure in the view-cell was measured by a Heise Digital Pressure Indicator. The temperature and pressure conditions that were tested are shown in Tables 1-3. Once the pressure reading was constant, stirring was stopped. The system was left to stabilize until the two phases (the soybean oil and the methanol) separated, which took approximately 30 minutes. Samples (250 μl) were then taken from the bottom of the view-cell utilizing a VICI sampling valve and were received directly in a vial that contained approximately 1.6 ml of 1,2-dichloroethane. This sample was analyzed for methanol and soybean oil by gas chromatography on a Hewlett Packard 6890 gas chromatograph, column Restek MXT-65TG, detector FID.

After removing the sample, the stirring was initiated and the pressure increased to the second desired pressure, and the procedure was repeated. For the second and subsequent sampling, the actual initial volume of both the soybean oil and methanol phases was estimated by visually inspecting phase levels and considering that the previous sampling removed about 0.25 ml of the contents of the view-cell. This testing gave a rapid estimate of phase behavior and relative adequacy of the different gases to improve the dissolution of the methanol in the soybean oil phase.

Control experiments were performed in a closed cell under the system's own vapor pressure starting at an initial methanol:oil ratio of 1:1. In the control experiments, the concentration of methanol in the soybean oil phase was below 2 wt % at 60° C. and at 120° C.

When carbon dioxide was utilized to pressurize the system, a bottom phase (mostly soybean oil) and a top phase (mostly methanol) were seen under all temperature and pressure conditions applied. The concentration of the methanol in the soybean oil phase ranged between 5 wt % and 22 wt %, as shown in Table 1. However, using the carbon dioxide at higher temperatures and pressures showed an improvement in the solubility of the methanol phase in the soybean oil phase compared to the control experiments, which showed a concentration of methanol in the soybean oil of less than 2%. As such, the presence of the carbon dioxide in the system improved the concentration of the methanol in the soybean oil.

TABLE 1

Effect of Carbon Dioxide as the Expanding Gas.

| Temperature (° C.) | Approximated Initial Methanol:Oil Ratio (volume/volume)[1] | Carbon Dioxide Pressure (psig) | Concentration of Methanol in Oil Layer wt methanol/(wt methanol + wt oil) * 100 |
|---|---|---|---|
| 60 | 1 | 323 | 5 |
| 60 | 2 | 611 | 9 |
| 60 | 3 | 1009 | 21 |
| 80 | 1 | 288 | 12 |
| 80 | 2 | 430 | 10 |
| 80 | 2 | 628 | 13 |
| 80 | 3 | 1027 | 19 |
| 100 | 2 | 436 | 11 |
| 100 | 2 | 626 | 15 |
| 100 | 3 | 906 | 22 |
| 120 | 1 | 299 | 7 |
| 120 | 2 | 433 | 19 |
| 120 | 3 | 633 | 22 |

[1]The initial cell volume was filled with 50% by volume soybean oil and 50% by volume methanol. Accounting for the different densities of methanol and soybean oil (0.795 g/cm$^3$ and 0.92 g/cm$^3$, respectively), the view-cell initially included 0.86:1 by weight of methanol:soybean oil. Since the sampling removed methanol and soybean oil, the approximate methanol:oil ratios at later points in the experiment were estimated as indicated in Table 1.

When propane was utilized as the expanding gas at temperatures between 60° C. and 120° C., a pressure of approximately 400 psig and above produced expansion of the soybean oil phase and improved the dissolution of methanol in the soybean oil phase, as shown in Table 2. The results show that a methanol concentration of greater than 20 wt % in the soybean oil phase was obtained by utilizing propane as the expanding gas at medium pressures. Almost complete dissolution of the methanol in the soybean oil phase was obtained at 120° C. when starting from a methanol:oil ratio of 2:1 and 3:1 and pressures of 628 psig and 836 psig. The propane gas was used to expand both the soybean oil and the methanol phases, allowing a single phase to form.

TABLE 2

Effect of Propane as the Expanding Gas.

| Temperature (° C.) | Approximated Initial Methanol:Oil Ratio (volume/volume)[1] | Propane Pressure (psig) | Concentration of Methanol in Oil Layer wt methanol/(wt methanol + wt oil) * 100 |
|---|---|---|---|
| 60 | 1 | 223 | 14 |
| 60 | 2 | 430 | 18 |
| 60 | 2 | 599 | 23 |
| 60 | 3 | 927 | 32 |
| 80 | 1 | 289 | 13 |
| 80 | 2 | 443 | 20 |
| 80 | 2 | 635 | 20 |
| 80 | 3 | 997 | 34 |
| 100 | 1 | 284 | 9 |
| 100 | 2 | 450 | 34 |
| 100 | 2 | 632 | 46 |
| 100 | 3 | 1005 | 55 |
| 120 | 1 | 276 | 36 |
| 120 | 2 | 420 | 40 |
| 120 | 2 | 628 | 65 |
| 120 | 3 | 836 | 63 |

[1]The initial cell volume was filled with 50% by volume soybean oil and 50% by volume methanol. Accounting for the different densities of methanol and soybean oil (0.795 g/cm$^3$ and 0.92 g/cm$^3$, respectively), the view-cell initially included 0.86:1 by weight of methanol:soybean oil. Since the sampling removed methanol and soybean oil, the approximate methanol:oil ratios at later points in the experiment were estimated, as indicated in Table 2.

When ethane was utilized as the expanding gas at temperatures between 60° C. and 120° C., the expansion of the soybean oil phase was seen at 120° C. and at pressures greater than 400 psig, as shown in Table 3. A marked improvement in methanol solubility was obtained at a temperature of 120° C., at pressures of 600 psig or greater, and at initial methanol:soybean oil ratios of 2:1 and 3:1. For example, using an initial methanol:soybean oil ratio of approximately 3:1, a pressure of 988 psig produced the almost complete dissolution of methanol in the soybean oil phase at 120° C.

TABLE 3

Effect of Ethane as the Expanding Gas.

| Temperature (° C.) | Approximated Initial Methanol:Oil Ratio (volume/volume)[1] | Ethane Pressure (psig) | Concentration of methanol in oil layer wt methanol/(wt methanol + wt oil) * 100 |
|---|---|---|---|
| 60 | 1 | 303 | 17 |
| 60 | 2 | 429 | 21 |
| 60 | 2 | 636 | 12 |
| 60 | 3 | 906 | 14 |
| 60 | 3 | 1034 | 22 |
| 80 | 1 | 305 | 5 |
| 80 | 2 | 432 | 8 |
| 80 | 2 | 633 | 16 |
| 80 | 3 | 894 | 19 |
| 80 | 3 | 1009 | 22 |

TABLE 3-continued

Effect of Ethane as the Expanding Gas.

| Temperature (° C.) | Approximated Initial Methanol:Oil Ratio (volume/volume)[1] | Ethane Pressure (psig) | Concentration of methanol in oil layer wt methanol/(wt methanol + wt oil) * 100 |
|---|---|---|---|
| 100 | 1 | 293 | 10 |
| 100 | 2 | 432 | 31 |
| 100 | 2 | 633 | 6 |
| 100 | 3 | 876 | 19 |
| 100 | 3 | 960 | 23 |
| 120 | 1 | 304 | 2 |
| 120 | 2 | 438 | 26 |
| 120 | 2 | 634 | 59 |
| 120 | 3 | 894 | 70 |
| 120 | 3 | 988 | 75 |

[1]The initial cell volume was filled with 50% by volume soybean oil and 50% by volume methanol. Accounting for the different densities of methanol and soybean oil (0.795 g/cm$^3$ and 0.92 g/cm$^3$, respectively), the view-cell initially included 0.86:1 by weight of methanol:soybean oil. Since the sampling removed methanol and soybean oil, the approximate methanol:oil ratios at later points in the experiment were estimated, as indicated in Table 3.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A method of producing an alkyl ester, comprising:
   providing a reaction mixture in a liquid phase, the reaction mixture comprising an alcohol and a triglyceride or fatty acid;
   dissolving an expanding gas into the alcohol to render the alcohol substantially miscible with the triglyceride or fatty acid; and
   reacting the alcohol with the triglyceride or fatty acid in the liquid phase to produce an alkyl ester.

2. The method of claim 1, wherein providing the reaction mixture in the liquid phase comprises providing the alcohol and the triglyceride or fatty acid that are substantially immiscible at ambient temperature and pressure.

3. The method of claim 1, wherein dissolving the expanding gas into the alcohol comprises forming a gas expanded solvent.

4. The method of claim 1, wherein dissolving the expanding gas into the alcohol comprises dissolving the expanding gas into an alcohol selected from the group consisting of methanol, ethanol, propanol, butanol, isomers thereof, and mixtures thereof.

5. The method of claim 1, wherein dissolving the expanding gas into the alcohol comprises dissolving a nonpolar expanding gas into the alcohol.

6. The method of claim 5, wherein dissolving the nonpolar expanding gas into the alcohol comprises dissolving a nonpolar expanding gas selected from the group consisting of carbon dioxide, methane, ethane, propane, butane, pentane, ethylene, propylene, butylene, pentene, isomers thereof, and mixtures thereof into the alcohol.

7. The method of claim 1, wherein dissolving the expanding gas into the alcohol comprises dissolving from approximately 1% to approximately 20% of the expanding gas into the alcohol.

8. The method of claim 1, wherein dissolving the expanding gas into the alcohol comprises maintaining the reaction mixture at a temperature below, at, or above a critical temperature of the expanding gas and at a pressure below, at, or above a critical pressure of the expanding gas.

9. The method of claim 1, wherein dissolving the expanding gas into the alcohol comprises maintaining the reaction mixture at a temperature ranging from approximately 10° C. to approximately 200° C.

10. The method of claim 1, wherein dissolving the expanding gas into the alcohol comprises maintaining the reaction mixture at a pressure ranging from approximately 200 pounds per square inch gauge to approximately 5,000 pounds per square inch gauge.

11. The method of claim 1, further comprising adjusting at least one of a temperature and a pressure to separate the alkyl ester from at least one of the expanding gas, glycerol, and excess alcohol.

12. The method of claim 11, wherein adjusting at least one of the temperature and the pressure to separate the alkyl ester from at least one of the expanding gas, glycerol, and excess alcohol comprises lowering at least one of the temperature and the pressure.

13. The method of claim 1, further comprising adjusting at least one of a temperature and a pressure to recover the expanding gas.

14. The method of claim 13, wherein adjusting at least one of the temperature and the pressure to recover the expanding gas comprises lowering at least one of the temperature and the pressure to ambient temperature and ambient pressure.

15. A method of producing an alkyl ester, comprising:
   dissolving an expanding gas into an alcohol to form a gas expanded solvent, wherein the alcohol of the gas expanded solvent is nonpolar;
   contacting the gas expanded solvent with a triglyceride or a fatty acid; and
   reacting the alcohol and the triglyceride or fatty acid in a liquid phase to form an alkyl ester.

16. The method of claim 15, wherein dissolving the expanding gas into the alcohol comprises dissolving the expanding gas into an alcohol selected from the group consisting of methanol, ethanol, propanol, butanol, isomers thereof, and mixtures thereof.

17. The method of claim 15, wherein dissolving the expanding gas into the alcohol comprises dissolving a nonpolar expanding gas into the alcohol.

18. The method of claim 17, wherein dissolving the nonpolar expanding gas into the alcohol comprises dissolving a nonpolar gas selected from the group consisting of carbon dioxide, methane, ethane, propane, butane, pentane, ethylene, propylene, butylene, pentene, isomers thereof, and mixtures thereof into the alcohol.

19. The method of claim 15, wherein reacting the alcohol and the triglyceride or fatty acid in a liquid phase to form the alkyl ester comprises formulating the alcohol and the triglyceride or fatty acid to be miscible with one another.

20. The method of claim 15, wherein dissolving the expanding gas into the alcohol comprises maintaining the expanding gas and the alcohol at a temperature below, at, or above a critical temperature of the expanding gas and at a pressure below, at, or above a critical pressure of the expanding gas.

21. The method of claim 15, wherein dissolving the expanding gas into the alcohol comprises maintaining the expanding gas and the alcohol at a temperature ranging from approximately 10° C. to approximately 200° C.

22. The method of claim 15, wherein dissolving the expanding gas into the alcohol comprises maintaining the expanding gas and the alcohol at a pressure ranging from approximately 200 pounds per square inch gauge to approximately 5,000 pounds per square inch gauge.

23. The method of claim 15, further comprising adjusting at least one of the temperature and pressure to separate the alkyl ester from at least one of the expanding gas, glycerol, and excess alcohol.

24. The method of claim 23, wherein adjusting at least one of the temperature and pressure to separate the alkyl ester from at least one of the expanding gas, glycerol, and excess alcohol comprises lowering at least one of the temperature and pressure.

25. The method of claim 15, further comprising adjusting at least one of the temperature and pressure to recover the expanding gas.

26. The method of claim 25, wherein adjusting at least one of the temperature and pressure to recover the expanding gas comprises lowering at least one of the temperature and pressure to ambient temperature and ambient pressure.

* * * * *